(12) United States Patent
Schroering

(10) Patent No.: US 6,419,492 B1
(45) Date of Patent: Jul. 16, 2002

(54) DENTAL IMPLANT SYSTEM INCORPORATING AN EXTERNAL HEX AND MORSE TAPERED WALLS

(76) Inventor: Robert L. Schroering, 3950 Kresge Way, Suite 403, Louisville, KY (US) 40207

( * ) Notice: Subject to any disclaimer, the term of this patent is extended or adjusted under 35 U.S.C. 154(b) by 0 days.

(21) Appl. No.: 09/855,351

(22) Filed: May 15, 2001

Related U.S. Application Data

(60) Provisional application No. 60/204,320, filed on May 15, 2000.

(51) Int. Cl.[7] .................................................. A61C 8/00
(52) U.S. Cl. ...................................................... 433/173
(58) Field of Search .................................. 433/172, 173, 433/174, 177

(56) References Cited

U.S. PATENT DOCUMENTS

| | | | |
|---|---|---|---|
| 4,713,003 A | 12/1987 | Symington et al. | |
| 4,713,004 A | 12/1987 | Linkow et al. | |
| 4,738,623 A | * 4/1988 | Driskell | 433/173 |
| 5,106,300 A | * 4/1992 | Voitik | 433/173 |
| 5,427,527 A | 6/1995 | Niznick et al. | |
| 5,433,606 A | 7/1995 | Niznick et al. | |
| 5,591,029 A | 1/1997 | Zuest | |
| 5,601,429 A | 2/1997 | Blacklock | |
| 5,685,715 A | 11/1997 | Beaty et al. | |
| 5,695,336 A | 12/1997 | Lazzara et al. | |
| 5,709,547 A | 1/1998 | Lazzara et al. | |
| 5,727,943 A | 3/1998 | Beaty et al. | |
| 5,755,574 A | 5/1998 | D'Alise | |
| 5,863,201 A | 1/1999 | Lazzara et al. | |
| 5,885,079 A | 3/1999 | Niznick | |
| 6,203,324 B1 | * 3/2001 | Wils | 433/173 |

* cited by examiner

Primary Examiner—Cary O'Connor
(74) Attorney, Agent, or Firm—Joan L. Simunic; Middleton Reutlinger

(57) ABSTRACT

A dental implant system having an implant and an coordinating abutment is described. The implant includes an hexagonal reference post against which a prosthesis can be keyed and a Morse-tapered cavity wall. The abutment is adapted to engage the implant cavity wall and can be indexed relative to the implant. In an alternative embodiment, the post within the implant is provided as a separate piece which fits snuggly within the implant.

11 Claims, 4 Drawing Sheets

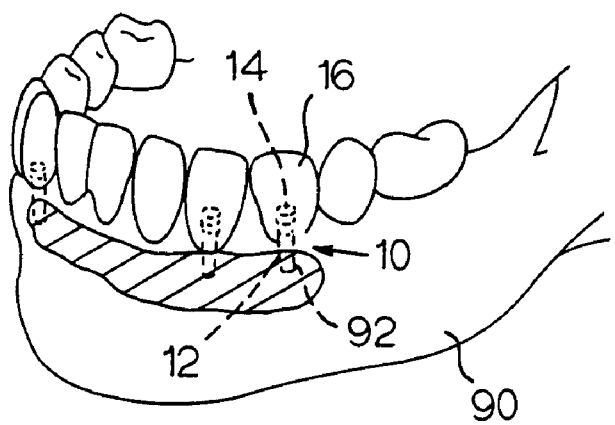
FIG. 1
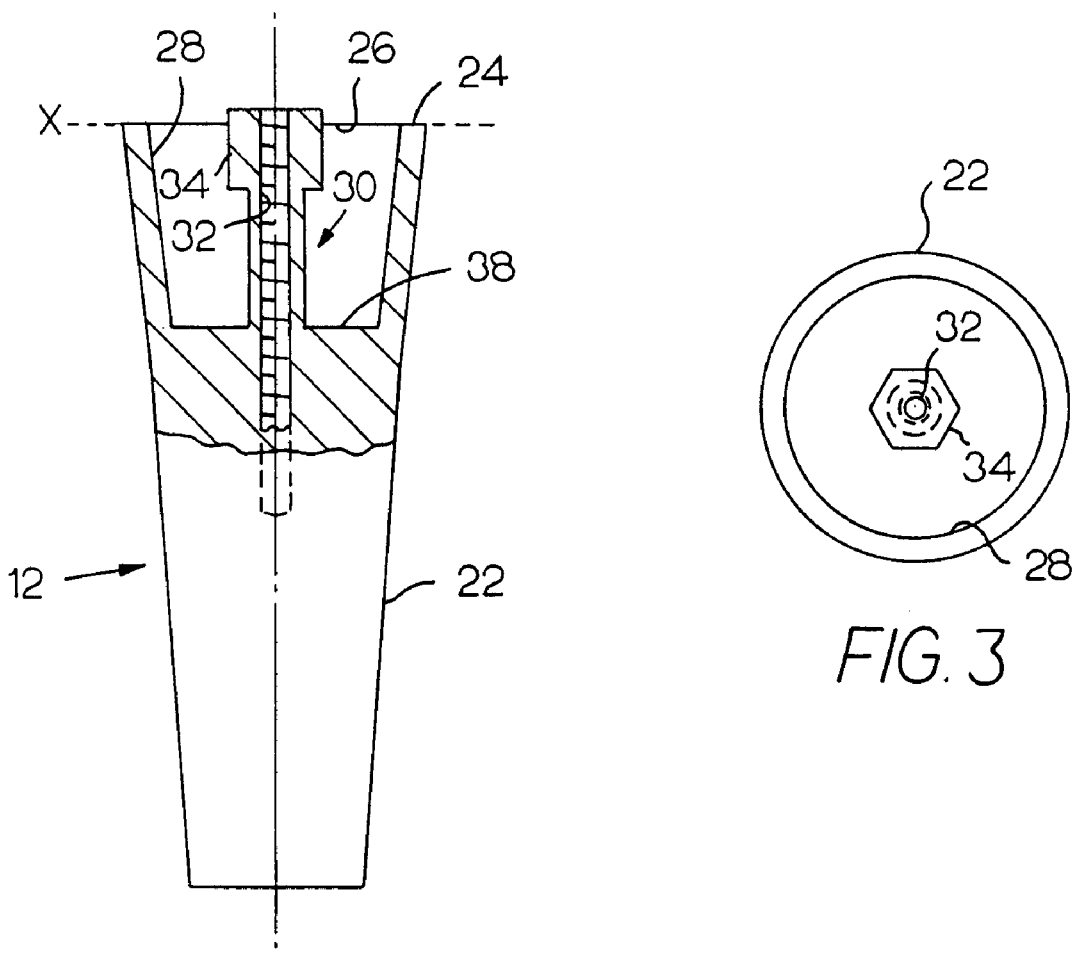
FIG. 2
FIG. 3

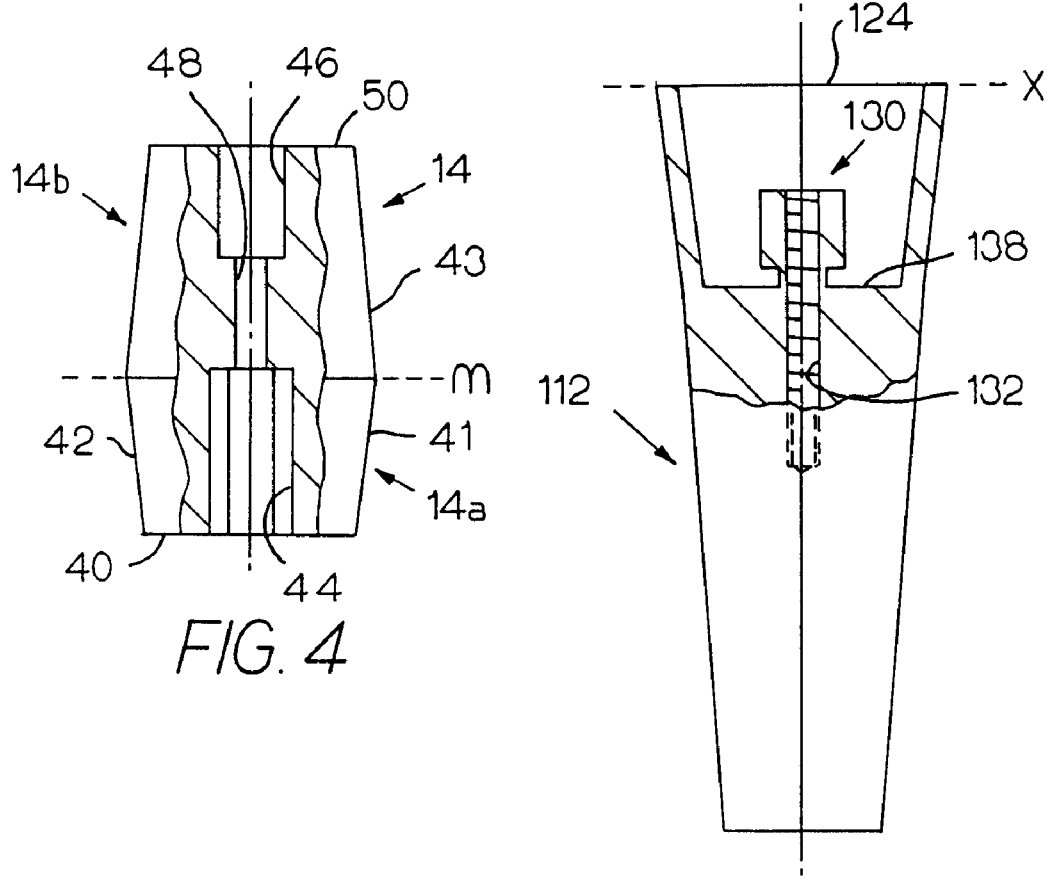
FIG. 4
FIG. 5
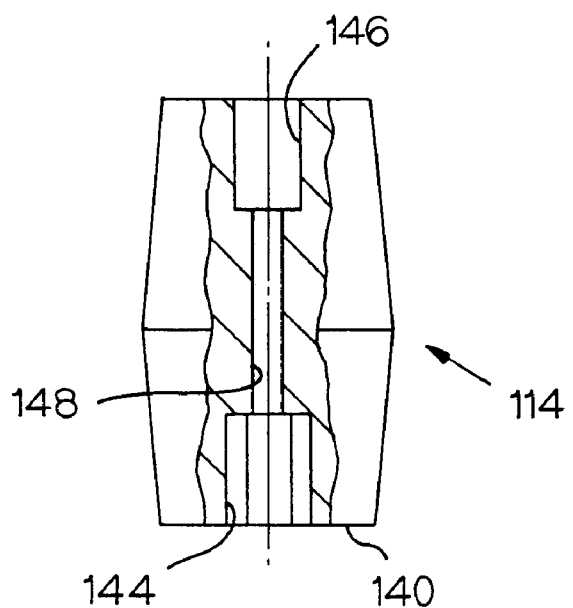
FIG. 6

DENTAL IMPLANT SYSTEM INCORPORATING AN EXTERNAL HEX AND MORSE TAPERED WALLS

CROSS-REFERENCE TO RELATED APPLICATIONS

This application claims priority from U.S. Provisional Application Ser. No. 60/204,320, filed May 15, 2000, which is incorporated herein by reference in its entirety.

BACKGROUND

The present invention relates to a dental implant system that includes an implant and an abutment. The implant has internal Morse-tapered walls and the abutment has an external hex for indexing prostheses and exterior Morse tapered walls to reduce the risk of abutment loosening.

Dental implants are embedded in the jaw bone and serve to anchor one or more artificial teeth, or prostheses. Initially the implant is secured within the jaw bone, then the artificial tooth is anchored to the implant. Typically, the artificial tooth is inserted in a multi-step process that includes initially attaching an abutment to the implant, and then cementing a crown on the abutment.

Because the artificial tooth must be in a specific alignment within the mouth to be consistent with the other teeth, it is beneficial to have a reference on the implant against which the artificial tooth can be keyed or aligned. Ideally, once the artificial tooth is keyed to the reference of the implant, the tooth will not be able to reorient itself within the mouth during common use. However, clinical studies have shown that even with a reference on the implant the commonly used straight wall abutment can rotate slightly, thereby allowing the prosthesis to become misaligned. Thus, it would be beneficial to have a dental implant that could index the prosthesis with little probability that the implant or abutment would rotate after positioning in the mouth.

SUMMARY OF THE INVENTION

The present invention relates to a dental implant system having an implant with an hexagonal reference post against which a prosthesis can be keyed and a Morse-tapered cavity wall, and having an abutment adapted to coordinate with the implant cavity wall and that can be indexed relative to the implant and that has a Morse tapered external wall. The abutment fits within the implant with the external wall of the abutment mating with the cavity wall of the implant, and is aligned with the hexagonal post of the implant or the adapter. The prosthesis is then secured to the abutment. The hexagonal post functions to align the abutment initially, and the Morse tapering of the walls function to secure the abutment to the implant, thereby preventing the prosthesis from twisting during normal use. In an alternative embodiment, the post within the implant is provided as a separate piece which fits snuggly within the implant.

DESCRIPTION OF FIGURES

FIG. 1 is a perspective view of a dental implant system made in accordance with the present invention anchored in a lower jaw bone;

FIG. 2 is a side cross-sectional view of the dental implant of FIG. 1;

FIG. 3 is a top view of the dental implant of FIG. 1;

FIG. 4 is a side cross-sectional view of the abutment of FIG. 1;

FIG. 5 is a side cross-sectional view of a first alternative embodiment of the dental implant of FIG. 2;

FIG. 6 is a side cross-sectional view of a first alternative embodiment of the abutment of FIG. 4;

DETAILED DESCRIPTION OF THE INVENTION

Figure 7:
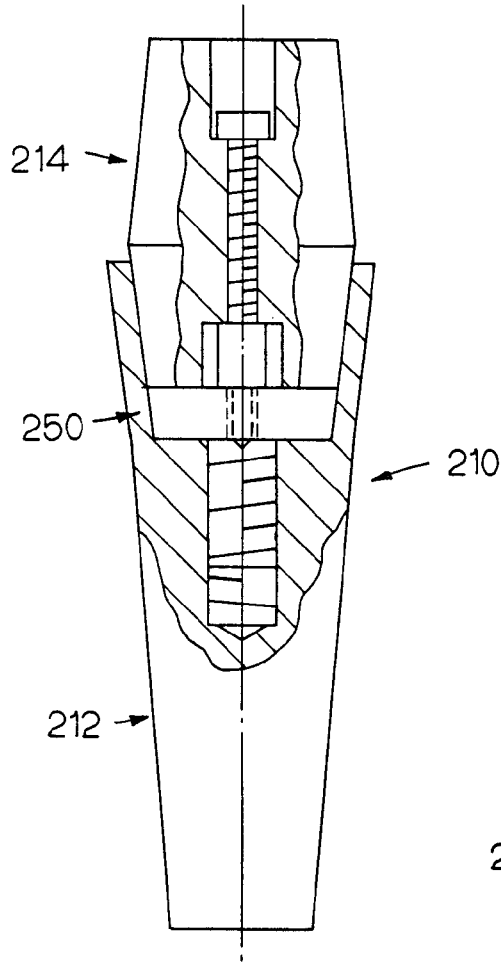
FIG. 7 is a side cross-sectional view of a first alternative embodiment of the dental implant system of FIG. 1.

The dental implants depicted in the various Figures are selected solely for the purposes of illustrating the invention. Other and different dental implants may utilize the inventive features described herein as well.

Reference is first made to FIGS. 1–4 in which a dental implant system constructed in accordance with the present invention is generally noted by the character numeral 10, and includes as major components a dental implant 12, an abutment 14, and a prosthesis 16. As shown in FIG. 1, the implant system 10 is mounted in a cavity 92 bored into the jaw bone 90 of the patient such that the implant 12 extends into the jaw bone 90. After the implant 12 is anchored in the jaw bone 90, the abutment 14 is secured to the implant 12, and a prosthesis or artificial tooth 16 can be secured to the abutment 14 as is known in the art. The implant 12, shown in greater detail in FIG. 2, can be formed from any smooth hard material commonly known in the art as being suitable for dental implants; and the body 22 exterior may have a threaded or porous beaded surface, as is known in the art. In a preferred embodiment, the implant 12 is machined from a titanium alloy, and the body 22 has a threaded exterior surface.

As shown in FIGS. 2 and 3, the head 24 of the implant 12 defines a cavity or well 26, having a side wall 28 and a base 38, with an anchoring post 30 positioned at essentially the center of the well 26. The taper angle of the exterior side wall 28 of the well 26 is a Morse taper, i.e. a taper angle of less than about 8°. In the embodiment of FIGS. 1–4 the taper angle of the exterior side wall 28 is approximately 7°. The anchoring post 30 projects from essentially the center of the well 26 toward the head 24. The post 30 includes a threaded core 32, which can receive a screw passed through the abutment 14, thereby attaching the abutment 14 to the implant 12. The exterior of the post 30 includes a hexagonal-shaped tip 34 that preferably projects just slightly above the plane X which defines the top 24 of the implant 12. The lower section of the post 30 can also be hexagonal-shaped (not shown) or may be circular, as shown.

As shown in FIG. 4, the abutment 14 has a base 40 and a top 50, and defines an exterior wall 42, a first internal cavity 44, a second internal cavity 46, and a channel 48. The abutment 14 is divided into two sections—a lower section 14a and an upper section 14b—by a midline "m". The lower section 14a defines an exterior wall 41 which fits within the well 26 of the implant 12. In the embodiment of FIGS. 1–4, the taper angle of the implant wall 41 is preferably a Morse taper, so that the implant wall 41 mates with the exterior side wall 28. The upper section 14b defines an exterior wall 43 that can have any angle that will allow the prosthesis 16 to be securely attached. The first internal cavity 44 is in the lower section 14a of the abutment 14 and protrudes into the abutment 14 from the base 40. The cavity 44 has a hexagonal shape and is adapted to fit over the post 30. In the embodiment of FIGS. 1–4, the cavity 44 extends from the base 40 to slightly beyond the midline "m", so that when the abutment 14 is positioned in the implant 12, the base 40 is flush with the well base 38. The second internal cavity 46 is in the upper section 14b and protrudes into the abutment 14 from the top 50. It 46 is adapted to accept the head of a screw. The channel 48 connects the first and second cavities 44, 46. When the abutment 14 is used with the implant 12, the first internal cavity 44 of the abutment 14 is positioned over the anchoring post 30 so that the hexagonal tip 34 is aligned with the hexagonal shape of the cavity 44 and the implant wall 41 is flush against the exterior side wall 28. A screw is then passed into the second internal cavity 46 and through the channel 48 into the threaded core 32 of the implant 12, thereby securing the abutment 14 to the implant 12. In the embodiment of FIGS. 1–4, implant wall 41 is long enough that when the abutment 14 is secured to the implant 12 with the screw the bottom 40 of the abutment 14 lies essentially flush against the base 38 of the implant well 26. The combination of the Morse tapered walls and the flush base 38 to bottom 40 fit prevent contaminants from entering the void that remains between the post 30 and the first cavity 44.

FIG. 5 shows an implant 112 and FIG. 6 shows an abutment 114 which are essentially identical to the implant 12 and abutment 14, respectively, except that the post 130 and first internal cavity 144 have been shortened so that the top of the post 130 lies below the plane X which defines the top 124 of the implant 112. Similar to the embodiment of FIGS. 2–4, when the abutment 114 is used with the implant 112, the first internal cavity 144 of the abutment 114 is positioned over the post 130 and a screw is passed into a second internal cavity 146 and through a channel 148 into a threaded core 132 of the implant 112, thereby securing the abutment 114 to the implant 112. In the embodiment of FIGS. 5 and 6, when the abutment 114 is secured to the implant 112 with the screw, the bottom 140 of the abutment 114 lies essentially flush against the base 138 of the implant well 126.

Figure 8:
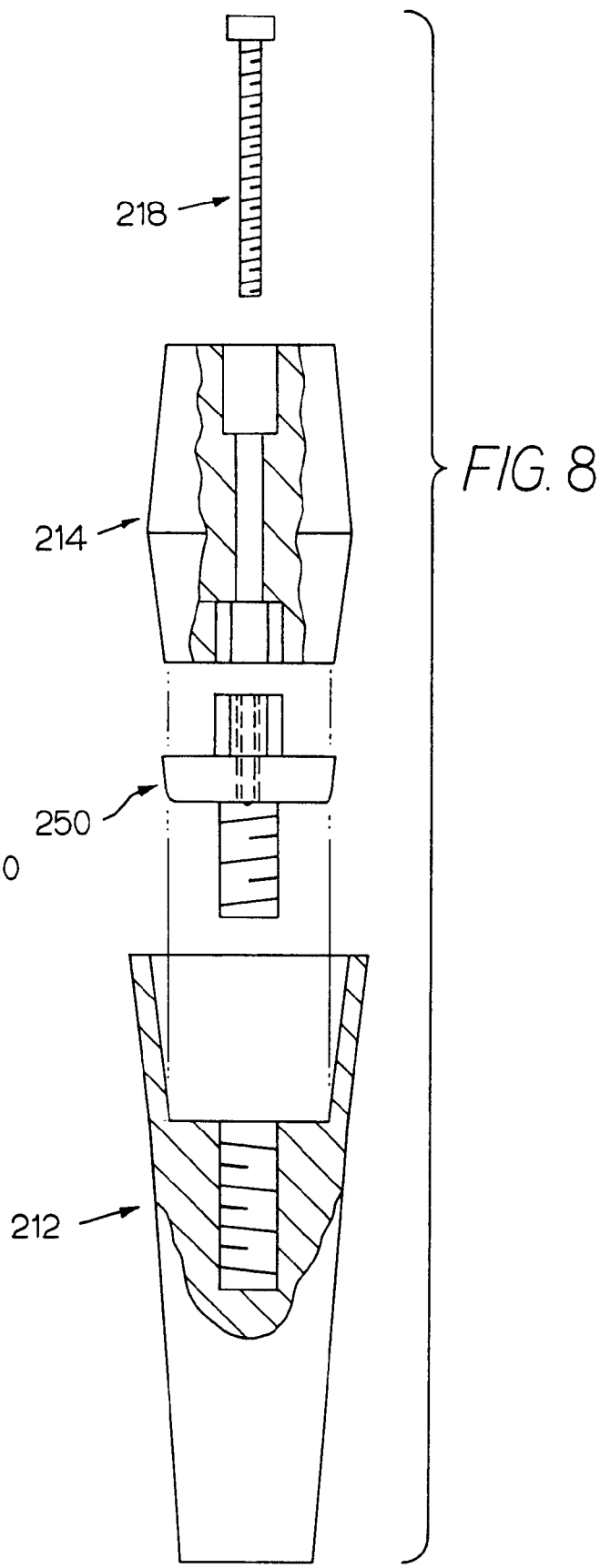
FIG. 8 is an exploded side view of the dental implant system of FIG. 7.

Alternatively, as shown in FIGS. 7–11, the dental implant system 210 may include an abutment 214 and a two-piece dental implant unit having an adapter 250 and an implant 212. When the two-piece implant unit is used, the dental implant system 210 is assembled as shown in FIGS. 7 and 8, with the implant 212 being secured into the patient's jawbone 90 (as in FIG. 1), the adapter 250 fitting into the implant 212, then the abutment 214 fitting onto the adapter 250, and a screw 218 securing the system 210 together.

Figure 9:
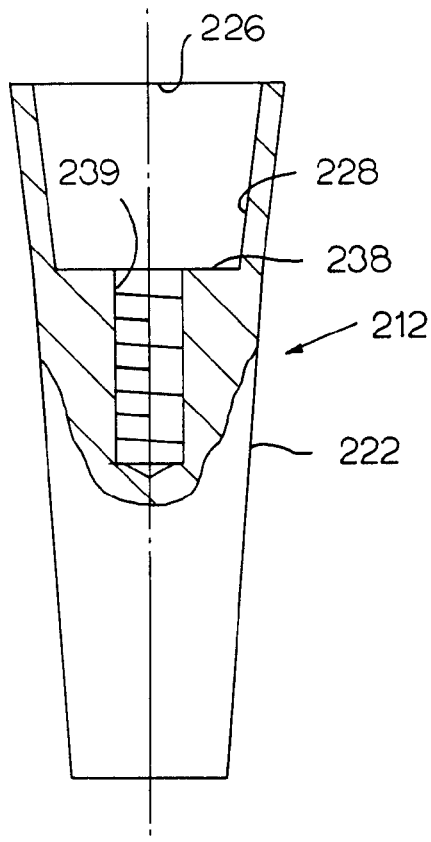
FIG. 9 is a side cross-sectional view of the dental implant of FIG. 7.

As shown in FIG. 9, the implant 212 defines a well 226, having a side wall 228 and a base 238, with a threaded cavity 239 protruding into the body 222 of the implant from the base 238. In the embodiment of FIGS. 7–11, the taper angle of the exterior side wall 228 of the well 226 is preferably a Morse taper, i.e. a taper angle of less than about 8°, and most preferably the taper angle of the exterior side wall 228 is approximately 7°. The implant 212 can be formed from any smooth hard material commonly known in the art as being suitable for dental implants; and the body 222 exterior may have a threaded or porous beaded surface, as is known in the art. In the embodiment of FIGS. 7–11, the implant 212 is machined from a titanium alloy, and the body 222 has a threaded exterior surface.

Figure 10:
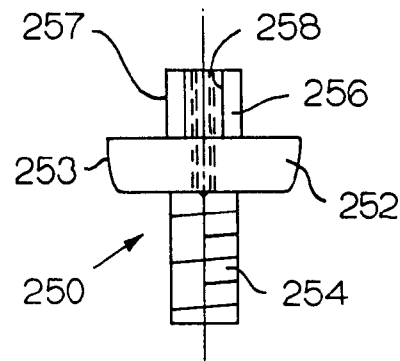
FIG. 10 is a side cross-sectional view of the adapter of FIG. 7.

The adapter 250, shown in FIG. 10, includes a body 252, a threaded post 254, and an indexing post 256. The threaded post 254 is proportioned to fit within the threaded cavity 239 of the implant 212 such that, when the adapter 250 is tightly screwed into the implant 212, the body 252 rests against the base 238 of the implant 212. The body 252 preferably has an exterior side wall 253 with a Morse taper, so that when the adapter 250 is secured in the implant 212, the side wall 253 of the body has a secure fit against the side wall 228 of the well 226. The indexing post 256 projects from the body 252 directly opposite the threaded post 254. The indexing post 256 has a threaded cavity 258 adapted to receive and secure the screw 218, and has an exterior walls 257 with a shaped periphery that can be used to align the abutment 214. In the embodiment of FIGS. 7–11, the walls 257 have a hexagonal shape.

Figure 11:
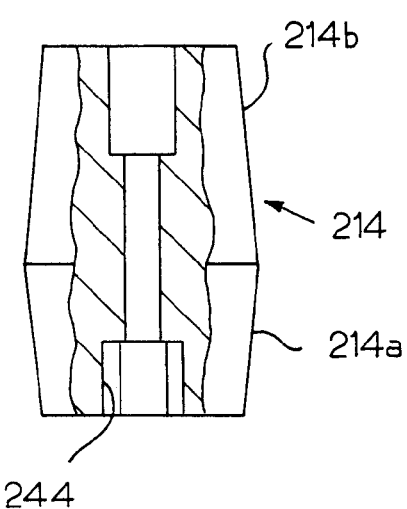
FIG. 11 is a side cross-sectional view of the abutment of FIG. 7.

As shown in FIG. 11, the abutment 214 is essentially identical to the abutment 114 of FIG. 6, except that the lower section 214a of the abutment 214 and the first internal cavity 244 have been shortened slightly to allow space for the adapter 250 within the well 226 of the implant 212.

Referring again to FIG. 7, when the two-piece implant system is used the adapter 250 fits into the implant 212, then the abutment 214 fits onto the adapter 250, and a screw 218 secures the system 210 together. Because the implant 212 includes a well 226 with a Morse taper, and the adapter 250 and abutment 214 each have a Morse taper, the units 212, 250, 214 provide an extremely tight fit relative to each other so that food particles and other contaminants cannot enter the assembled implant. Moreover, because of the Morse taper a friction fit is created between the interior walls of the implant and the exterior walls of the abutment virtually eliminate loosening of the abutment. By including the indexing post 258 on the adapter, the abutment 214 can be aligned within the implant 212, and is held stable thereafter.

Figure 12:
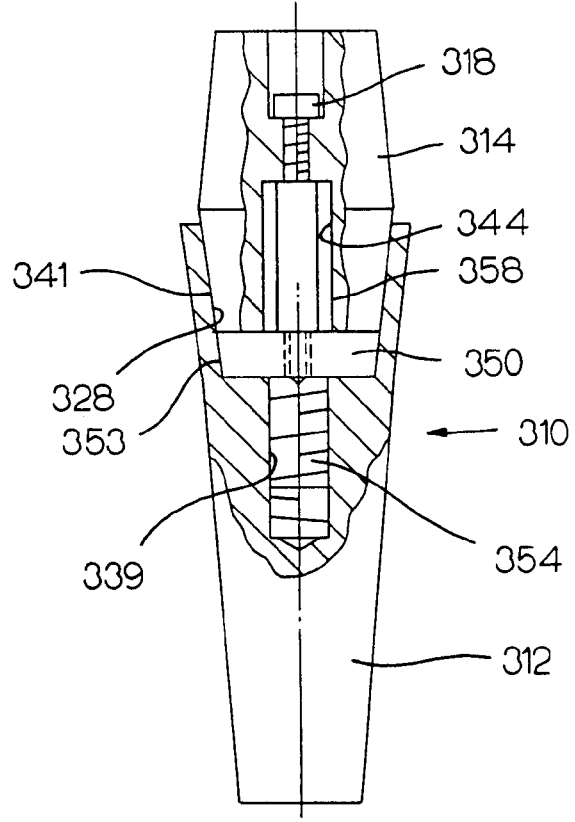
FIG. 12 is a side cross-sectional view of a second alternative embodiment of the dental implant system of FIG. 1.

An alternative design 310 for the implant/adapter/abutment system 210 is shown in FIG. 12. This implant system 310 has an implant 312, an adapter 350, an abutment 314, and a screw 318, and is essentially identical to the implant system 210 of FIG. 7, except that the indexing post 358 and the related first internal cavity 344 have been lengthened. Essentially, any length post and cavity can be used provided the combination allows for the base of the abutment to rest snuggly against the body of the adapter. Similarly, the length of the threaded post 354 and related cavity 339 may vary provided the combination allows for the adapter to rest snuggly within the implant. In all cases, the walls of the adapter 353 and/or the abutment 341 must also fit snuggly against the walls 328 of the implant 312.

Thus, the present development for a dental implant system incorporates both a reference for indexing the prosthesis and Morse tapered walls for reducing the risk of abutment loosening.

It is understood that, in light of a reading of the foregoing description and drawings, those with ordinary skill in the art will be able to make changes and modifications to the present invention without departing from the spirit or scope of the invention, as defined herein. For example, although the embodiments described herein include a screw to secure the various components to each other, other acceptable fastening means, including glues and adhesives, may be substituted.

What is claimed is:

1. A dental implant system for securing a prosthesis in a mouth, said system comprising of:

a. a prosthesis;

b. an abutment, adapted to receive said prosthesis, said abutment having a first internal cavity in communication with a second internal cavity, and said abutment having at least one exterior wall having a taper angle of less than about 8°; and c. an implant, defining a head and a body, said body adapted to be secured within a jawbone, and said head defining a cavity having side walls with a taper angle of less than about 8° adapted to matingly engage the exterior wall of said abutment, and said head having an anchoring post projecting into said implant cavity, said post including an indexing means adapted to engage said first abutment cavity.

2. The dental implant system of claim 1 wherein a channel connects the first and second cavities of said abutment.

3. The dental implant system of claim 2 wherein said implant post includes an internal channel adapted to receive a screw, and said abutment is secured to said implant by a screw projecting from the second abutment cavity through the abutment channel and into the post screw channel.

4. The dental implant system of claim 1 wherein said indexing means is a hexagonal shaped tip secured to said implant post.

5. The dental implant system of claim 4 wherein said first abutment cavity defines a hexagonal shape proportioned to engage said post tip.

6. A dental implant system for securing a prosthesis in a mouth, said system comprising of:

a. a prosthesis;

b. an abutment, adapted to receive said prosthesis, said abutment having a first internal cavity in communication with a second internal cavity, and said abutment having at least one exterior wall having a taper angle of less than about 8°; and c. an implant, comprising a body piece and a post piece, said body piece adapted to be secured within a jawbone and including a internal cavity having side walls with a taper angle of less than about 8° adapted to matingly engage the exterior wall of said abutment, and said post piece adapted to be secured to said body piece and including an anchoring post projecting into said implant cavity away from said body piece, said anchoring post including an indexing means adapted to engage said first abutment cavity.

7. The dental implant system of claim 6 wherein a channel connects the first and second cavities of said abutment.

8. The dental implant system of claim 7 wherein said implant post includes an internal channel adapted to receive a screw, and said abutment is secured to said implant by a screw projecting from the second abutment cavity through the abutment channel and into the post screw channel.

9. The dental implant system of claim 6 wherein said indexing means is a hexagonal shaped tip secured to said implant post.

10. The dental implant system of claim 9 wherein said first abutment cavity defines a hexagonal shape proportioned to engage said post tip.

11. The dental implant system of claim 6 wherein said implant post piece defines a wall having a taper angle of less than about 8° which can engage said body wall.

* * * * *